United States Patent
Aue et al.

(10) Patent No.: US 8,888,772 B2
(45) Date of Patent: Nov. 18, 2014

(54) ELECTROSURGICAL LAPAROSCOPIC INSTRUMENT HAVING AN ELECTRICAL LEAD

(75) Inventors: Thomas Aue, Wedel (DE); Hannes Miersch, Hamburg (DE)

(73) Assignee: Olympus Winter & IBE GmbH (DE)

( * ) Notice: Subject to any disclaimer, the term of this patent is extended or adjusted under 35 U.S.C. 154(b) by 222 days.

(21) Appl. No.: 13/639,606

(22) PCT Filed: Apr. 1, 2011

(86) PCT No.: PCT/EP2011/001654
§ 371 (c)(1),
(2), (4) Date: Feb. 27, 2013

(87) PCT Pub. No.: WO2011/124353
PCT Pub. Date: Oct. 13, 2011

(65) Prior Publication Data
US 2013/0150846 A1  Jun. 13, 2013

(30) Foreign Application Priority Data
Apr. 9, 2010  (DE) .......................... 10 2010 014 435

(51) Int. Cl.
*A61B 18/18* (2006.01)
*A61B 18/14* (2006.01)
*A61B 18/00* (2006.01)

(52) U.S. Cl.
CPC .......... *A61B 18/1482* (2013.01); *A61B 18/1445* (2013.01); *A61B 2018/00083* (2013.01)
USPC ............................................. 606/41

(58) Field of Classification Search
CPC ............... A61B 18/14; A61B 18/1482; A61B 18/1442; A61B 18/1445
USPC ............................................. 606/41
See application file for complete search history.

(56) References Cited

U.S. PATENT DOCUMENTS

| 5,766,170 A | 6/1998 | Eggers ........................... 606/48 |
| 5,846,240 A | 12/1998 | Kortenbach et al. ............. 606/48 |

(Continued)

FOREIGN PATENT DOCUMENTS

| DE | 201 18 302 | 1/2002 |
| DE | 10 2005 040 386 | 3/2007 |
| DE | 20 2009 007 592 | 9/2009 |
| EP | 2 263 550 | 12/2010 |
| WO | WO 2004/073490 | 9/2004 |

OTHER PUBLICATIONS

Office Action issued by German Patent Office on Dec. 21, 2010 in connection with corresponding application No. 10 2010 014 435.5-35.

(Continued)

*Primary Examiner* — Robert N Wieland
(74) *Attorney, Agent, or Firm* — Ostrolenk Faber LLP

(57) ABSTRACT

The invention relates to an electrosurgical laparoscopic instrument having an elongated shaft, wherein an end effector is disposed on the distal end of said shaft and a handle is disposed on the proximal end of said shaft. The shaft is designed as a tube through which a rod extends which is coupled to a movable part of the handle and to a movable part of the end effector for actuation by longitudinal movement, and the end effector is connected to the handle via at least one electrical lead. At least one of the leads is disposed in the wall of a hose which is disposed surrounding the rod in the tube.

4 Claims, 1 Drawing Sheet

(56) References Cited

U.S. PATENT DOCUMENTS 6,063,086 A  5/2000 Benecke et al. ................ 606/51
6,156,036 A  12/2000 Sussman
6,679,882 B1 * 1/2004 Kornerup ........................ 606/51

2010/0016855 A1  1/2010 Ramstein

OTHER PUBLICATIONS

International Search Report mailed Jul. 6, 2011 in corresponding PCT International Application No. PCT/EP2011/001654.

* cited by examiner

ELECTROSURGICAL LAPAROSCOPIC INSTRUMENT HAVING AN ELECTRICAL LEAD

CROSS-REFERENCE TO RELATED APPLICATIONS

The present application is a 35 U.S.C. §§371 national phase conversion of PCT/EP2011/001654, filed Apr. 1, 2011, which claims priority of German Patent Application No. 10 2010 014 435.5, filed Apr. 9, 2010, the contents of which are incorporated herein by reference. The PCT International Application was published in the German language.

BACKGROUND OF THE INVENTION

The invention relates to an electrosurgical laparoscopic instrument according to the preamble of claim 1.

A generic instrument is illustrated in DE 10 2005 040 386 A1. Here, the electrical leads are embodied as electrically conductive coatings of the conduit. This document also mentions that the practice is known of using the rod and the conduit as electrical conductors, or using an insulated cable laid in the interior of the conduit shaft.

All these design variants have significant disadvantages, particularly if there are frictional loads between conduit and rod. A cable running parallel to the rod in the conduit leads to a changing unsymmetrical contact between rod and conduit, leading to constantly changing handling conditions, which the user finds very irritating.

SUMMARY OF THE INVENTION

The object of the present invention consists of developing a generic instrument with a simpler design and constant handling conditions.

According to the invention, leads are arranged in the wall of a tube which is arranged surrounding the rod in the conduit, i.e. said tube is symmetrical all around with the wall thereof situated between rod and conduit. This relatively simple design avoids exotic and sensitive components such as electrically conductive wall coatings. The electrical leads are embedded, e.g. integrally cast, into the wall material of the tube. Like this they are well protected from friction between rod and conduit. Such a tube can be produced in a cost-effective fashion using techniques that are conventional for cable insulations. It can be embodied as surrounding the rod in a rotationally symmetric fashion with a constant wall thickness, and so there are always constant friction and handling conditions under all handling conditions. The design according to the invention is thus also suitable for forceps subjected to great loads which should apply great closing pressures and, in particular, also for forceps with a curved shaft in which the rod rests against the conduit with a great force in the curved part.

Provision is advantageously made for the features of claim 2. As a result it is possible to improve the friction between rod and conduit, which is of significant advantage, particularly in the case of transmitting high forces in a curved shaft, and substantially improves the operation and the controllability of the operation.

Provision is advantageously made for the features of claim 3. The tube can rest against the conduit or the rod in an immovable fashion, e.g. it can be secured by very high coefficients of friction or by adhesive bonding or the like. Movement then only occurs between the tube and the other shaft element, namely the rod or the conduit. As a result of this, the movement conditions and the friction conditions are devised more clearly and the electrical contacting problems at the ends of the tube are also simplified. By way of example, if the tube is fixedly connected to the conduit, the ends of the electrical leads are fixed with respect to the conduit. In the other case, the ends of the leads are fixed with respect to the rod if this is more advantageous for contacting purposes.

BRIEF DESCRIPTION OF THE DRAWINGS

The invention is illustrated in an exemplary and schematic fashion in the drawing. In detail.

DETAILED DESCRIPTION OF THE INVENTION

Figure 1:
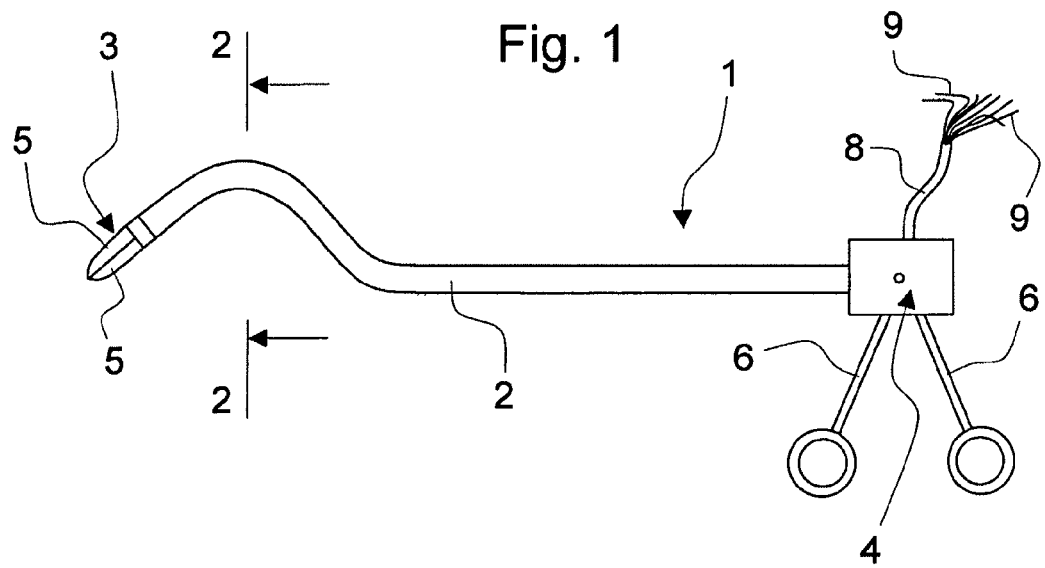
FIG. 1 shows a lateral view of an instrument according to the invention with a curved shaft.

FIG. 1 shows an electrosurgical laparoscopic instrument in the form of forceps 1 with an elongate shaft which is curved in the distal end region and embodied as a conduit 2, and with an end effector which is attached to the distal end of the conduit 2 and embodied as a pair of forceps jaws 3, and with a handle 4 which is attached to the distal end of the conduit 2.

The forceps jaws 3 have two jaw parts 5, which are illustrated in the closed state and can be swiveled with respect to one another. Mounted on the handle 4 there are two gripper parts 6 which are provided with the conventional finger rings and can be moved relative to one another.

Figure 2:
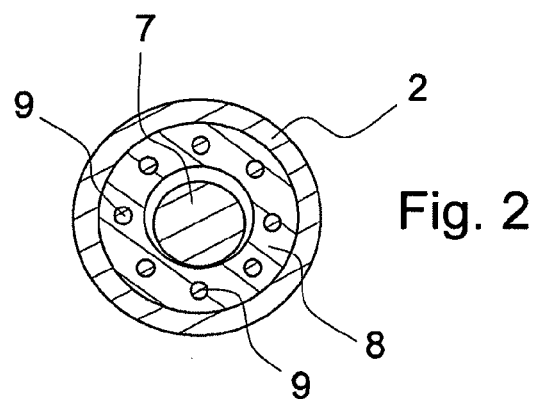
FIG. 2 shows a section according to line 2-2 in FIG. 1.

Via a rod 7 which is arranged in the interior of the conduit 2 and passes through the latter, which is illustrated in FIG. 2, in the longitudinal direction, the gripper parts 6 of the handle 4 are coupled to the rod jaws 3 for bringing about the relative movement of the jaw parts 5.

In the illustrated exemplary embodiment, the instrument is designed as a pair of forceps 1, with the jaw parts 5 being embodied as forceps branches. In an embodiment which has not been illustrated, the instrument can also be embodied as a pair of scissors, with the jaw parts 5 being embodied as scissor blades.

The illustrated forceps 1 can be embodied with a straight conduit 2 (not illustrated) which runs in a straight line between handle 4 and forceps jaws 3.

However, the conduit 2 in laparoscopic instruments of this type has a rigid design in any case.

In the illustrated exemplary embodiment, the forceps 1 are embodied for use with another laparoscopic instrument in a common port, as described in DE 20 2009 007 592 U. For the purposes presented in this document, it is necessary for the tube 2, as illustrated in FIG. 1, to have a curved design in the distal region thereof.

As already presented in the document cited at the outset, at least one electrode in the case of the forceps 1 is provided on the forceps jaws 3. Here, this can also be an embodiment with a plurality of electrodes which, e.g. in a multi-polar technique, should optionally be supplied in pulsed operation with different polarity.

In the illustrated exemplary embodiment, the two jaw parts 5 can be embodied as electrodes.

There may additionally be sensors such as e.g. thermal sensors which should likewise be supplied by electrical leads. In the case of the forceps 1 it may therefore be necessary to lay a relatively large number of electrical leads through the conduit 2.

To this end, as illustrated in FIG. 2, the invention provides a tube 8 which is arranged within the conduit 2, passes through the latter in the longitudinal direction, and surrounds the rod 7. By way of example, the tube 8 can be made of a suitable polymer, such as e.g. PTFE (polytetrafluoroethylene). A plurality of electrical leads 9—there are eight leads 9 (for explanatory purposes) in the drawing example in FIG. 2—are arranged, e.g. integrally cast, in a rotationally symmetric fashion in a cross section of the wall material of the tube 8.

In the exemplary embodiment of FIG. 2, the tube 8 is embodied as resting against the conduit 2 and having a little play with respect to the rod 7. Here, the tube 8 can be attached to the conduit 2, e.g. as a result of high friction or adhesive bonding or the like. Very good friction conditions are preferably selected with respect to the rod 7 such that there is little friction here.

As shown in FIG. 1, the section of FIG. 2 is selected at the point of great curvature of the conduit 2. In the case of a high closing pressure of the forceps 1, i.e. if the rod 7 must transfer high tensile forces, the rod 7 rests laterally against the conduit 2, as shown in FIG. 2. The tube 8 between rod 7 and conduit 2 can lead to expedient coefficients of friction here.

Figure 3:
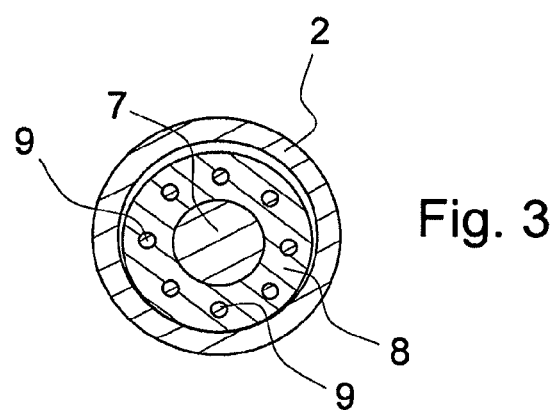
FIG. 3 shows a section corresponding to FIG. 2 through an embodiment variant.

FIG. 3 shows an embodiment variant in which the same reference signs are used. In contrast to the embodiment in FIG. 2, the tube 8 is embodied here as resting tightly against the rod 7 and having a little play with respect to the conduit 2.

As mentioned previously, the conduit 2 can, deviating from the embodiment in FIG. 1, have a straight embodiment. A design of the conduit 2 that can bend under pressure but remains sufficiently rigid during actuation is also feasible for these purposes.

The rod 7 can be a solid wire rod, but, particularly for the purposes of the curved conduit 2 in FIG. 1, it is better embodied as a wire coil, with (not illustrated) the rod 7 having a central wire core around which two wire coils are wound in opposite directions. Such a design can easily be bent and is also suitable for transmitting torques.

In an embodiment variant (not illustrated), the forceps jaws 3 can be embodied to be able to rotate with respect to the conduit 2. A rotation actuator by means of which the twist of the forceps jaws 3 is brought about should then be provided on the handle 4. The transmission of rotation from the handle 4 to the forceps jaws 3 can, for example, be brought about by the rod 7, which is then preferably embodied with cross-wound wire windings as mentioned above. However, the rotational actuation can advantageously also be brought about via the tube 8, which can be embodied with a suitable stiffness in respect of rotation, e.g. which can in turn be strengthened by cross-wound wire coils.

In the forceps jaws 3, electrodes, sensors and the like provided there are contacted by the leads 9 in the tube 8 in a suitable fashion. Depending on the design, it may in doing so be more advantageous to connect the tube 8 fixedly to the conduit 2 as per FIG. 2 or fixedly to the rod 7 as per FIG. 3.

By way of example, as shown in FIG. 1, the tube 8 can be guided laterally out of the handle 4 at the handle 4 in order to be routed on from there to a control and supply unit. It is also possible to provide plug-in contacts on the handle 4, which plug-in contacts are further connected to a plug and a connection cable (not illustrated).

In the illustrated exemplary embodiment all leads 9 running between forceps jaws 3 and handle 4 are arranged in the wall of the tube 8. However, in addition to the leads 9 provided in the tube 8, provision can also be made for differently embodied leads, e.g. in the form of electrically conductive coatings of the conduit 2. It is also possible to use the rod 7 and the conduit 2 as additional electrical conductors, or an insulated cable laid in the interior of the conduit 2 in addition to the tube 8.

The invention claimed is:

1. An electrosurgical laparoscopic instrument having an elongate shaft with an end effector arranged on the distal end of said shaft and a handle arranged on the proximal end of said shaft, the shaft being embodied as a conduit with a rod passing through it, said rod, for the purposes of actuation by a longitudinal movement, being coupled to a moveable part of the handle and to a moveable part of the end effector, and the end effector being connected to the handle by at least one electrical lead, wherein at least one of the leads is arranged in the wall of a tube which is arranged in the conduit surrounding the rod.

2. The instrument as claimed in claim 1, wherein the tube has low friction properties on one of its surfaces.

3. The instrument as claimed in claim 1, wherein the tube is embodied to rest against the conduit or the rod in an immovable fashion.

4. The instrument as claimed in claim 2, wherein the tube is embodied to rest against the conduit or the rod in an immovable fashion.

\* \* \* \* \*